US012793843B2

(12) United States Patent
Packer et al.

(10) Patent No.: US 12,793,843 B2
(45) Date of Patent: Nov. 10, 2026

(54) REAL-TIME EVALUATION OF CPR PERFORMANCE

(71) Applicant: ZOLL Medical Corporation, Chelmsford, MA (US)

(72) Inventors: Richard A. Packer, Westborough, MA (US); Gary A. Freeman, Waltham, MA (US); Christopher Luke Kaufman, Somerville, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 570 days.

(21) Appl. No.: 17/733,107

(22) Filed: Apr. 29, 2022

(65) Prior Publication Data

US 2022/0328182 A1 Oct. 13, 2022

Related U.S. Application Data

(63) Continuation of application No. 15/978,733, filed on May 14, 2018, now Pat. No. 11,348,686, which is a
(Continued)

(51) Int. Cl.
*A61B 5/00* (2006.01)
*A61B 5/0205* (2006.01)
(Continued)

(52) U.S. Cl.
CPC ........... *G16H 40/67* (2018.01); *A61B 5/0006* (2013.01); *A61B 5/0205* (2013.01);
(Continued)

(58) Field of Classification Search
CPC ..... A61B 5/0006; A61B 5/0205; A61B 5/044; A61B 5/7405; A61B 5/742; A61B 5/1135;
(Continued)

(56) References Cited

U.S. PATENT DOCUMENTS 6,292,692 B1 9/2001 Skelton et al.
6,351,671 B1 2/2002 Myklebust et al.
(Continued)

FOREIGN PATENT DOCUMENTS

CN 101365387 A 2/2009
CN 101835447 A 9/2010
(Continued)

*Primary Examiner* — Eugene T Wu
(74) *Attorney, Agent, or Firm* — The Webb Law Firm

(57) ABSTRACT

A computer-implemented method for providing summary information for lifesaving activities is disclosed. The method involves sensing one or more activities that are repeatedly and cyclically performed on a victim by a rescuer; identifying a cyclical timing interval over which performance is to be analyzed for a integer number of cycles of the one or more activities, and gathering data from the sensing of the one or more activities during the time interval; generating, from analysis of the one or more activities, summary data that condenses data sensed for the one or more activities into a summary of the one or more activities; and providing, for display to a user, a visual summary of the performance of the one or more activities over the identified time interval.

24 Claims, 7 Drawing Sheets

Related U.S. Application Data continuation of application No. 14/978,541, filed on Dec. 22, 2015, now Pat. No. 9,980,674, which is a continuation of application No. 14/284,545, filed on May 22, 2014, now Pat. No. 9,241,666, which is a continuation of application No. 13/295,781, filed on Nov. 14, 2011, now Pat. No. 8,738,129.

(60) Provisional application No. 61/413,336, filed on Nov. 12, 2010.

(51) Int. Cl.

| | |
|---|---|
| ***A61B 5/113*** | (2006.01) |
| ***A61B 5/33*** | (2021.01) |
| ***A61B 5/339*** | (2021.01) |
| ***A61N 1/39*** | (2006.01) |
| ***G16H 20/30*** | (2018.01) |
| ***G16H 20/40*** | (2018.01) |
| ***G16H 40/20*** | (2018.01) |
| ***G16H 40/63*** | (2018.01) |
| ***G16H 40/67*** | (2018.01) |
| *A61B 5/08* | (2006.01) |

(52) U.S. Cl.

CPC .............. *A61B 5/1135* (2013.01); *A61B 5/33* (2021.01); *A61B 5/339* (2021.01); *A61B 5/4836* (2013.01); *A61B 5/7405* (2013.01); *A61B 5/742* (2013.01); *A61N 1/3987* (2013.01); *G16H 20/30* (2018.01); *G16H 20/40* (2018.01); *G16H 40/20* (2018.01); *G16H 40/63* (2018.01); *A61B 5/08* (2013.01)

(58) Field of Classification Search

CPC ..... A61B 5/4836; A61N 1/3987; G06F 19/00; G16H 40/63; G16H 20/40

See application file for complete search history.

(56) References Cited

U.S. PATENT DOCUMENTS

| | | | | |
|---|---|---|---|---|
| 8,738,129 | B2 | 5/2014 | Packer et al. | |
| 2004/0006290 | A1 | 1/2004 | Sherman et al. | |
| 2004/0082888 | A1 | 4/2004 | Palazzolo et al. | |
| 2004/0122476 | A1 | 6/2004 | Wung | |
| 2006/0173501 | A1 * | 8/2006 | Stickney .............. | A61H 31/005 607/5 |
| 2008/0171311 | A1 | 7/2008 | Centen et al. | |
| 2008/0176199 | A1 | 7/2008 | Stickney et al. | |
| 2008/0312565 | A1 | 12/2008 | Celik-Butler et al. | |
| 2009/0024175 | A1 * | 1/2009 | Freeman .............. | G09B 23/288 607/6 |
| 2009/0035740 | A1 | 2/2009 | Reed et al. | |
| 2009/0240295 | A1 * | 9/2009 | Kellum ................ | A61N 1/3993 607/5 |
| 2010/0022886 | A1 | 1/2010 | Ayati et al. | |
| 2010/0211127 | A1 * | 8/2010 | Eerden ............... | A61N 1/39044 601/41 |
| 2011/0117529 | A1 | 5/2011 | Barash et al. | |
| 2011/0224565 | A1 | 9/2011 | Ong et al. | |

FOREIGN PATENT DOCUMENTS

| | | | | |
|---|---|---|---|---|
| EP | 1933114 | A1 | 6/2008 | |
| GB | 2344529 | B | 12/2002 | |
| JP | 2000176025 | A | 6/2000 | |
| JP | 2004280807 | A | 10/2004 | |
| JP | 2006503659 | A | 2/2006 | |
| JP | 2008529714 | A | 8/2008 | |
| JP | 2008534083 | A | 8/2008 | |
| JP | 2008250291 | A | 10/2008 | |
| WO | 2009037621 | A2 | 3/2009 | |
| WO | WO-2009039621 | A2 * | 4/2009 | .............. A47L 11/24 |

* cited by examiner

| Interval | Rate | Depth | Grade | Perfusion |
|---|---|---|---|---|
| 5 | 110 | 2.0 | A | 90% |
| 4 | 105 | 3.0 | B | 94% |
| 3 | 103 | 1.0 | C | 93% |
| 2 | 115 | 1.5 | B | 90% |
| 1 | 95 | 2.5 | C | 92% |

REAL-TIME EVALUATION OF CPR PERFORMANCE

CROSS-REFERENCE TO RELATED APPLICATIONS

This application is a continuation of U.S. patent application Ser. No. 15/978,733, filed May 14, 2018, which is a continuation of U.S. patent application Ser. No. 14/978,541, filed Dec. 22, 2015, now issued as U.S. Pat. No. 9,980,674, which is a continuation of U.S. patent application Ser. No. 14/284,545, filed May 22, 2014, now issued as U.S. Pat. No. 9,241,666, which is a continuation of U.S. patent application Ser. No. 13/295,781, filed Nov. 14, 2011, now issued as U.S. Pat. No. 8,738,129, which claims benefit of priority to U.S. Provisional Application No. 61/413,336, filed on Nov. 12, 2010, entitled "Real-Time Evaluation of CPR Performance," the entire contents of each of which are hereby incorporated by reference in their entireties.

TECHNICAL FIELD

This document relates to computer-based systems and techniques for analyzing performance of a rescuer in performing CPR and other related lifesaving techniques.

BACKGROUND

Sudden cardiac arrest (colloquially "heart attack") is a regular killer. The best treatment for cardiac arrest is quick and competent chest compressions to keep blood flowing through a victim's heart. Generally, every minute of delay in treating a cardiac arrest victim lowers the chance of survival by about ten percent. As a result, the ability to provide CPR in a competent manner can be a very important personal skill, and is particularly important for professional health-care workers such as emergency medical technicians (EMTs).

Various CPR feedback devices are available that indicate to a rescuer whether they are performing CPR chest compressions at an appropriate rate and an appropriate depth of compression, such as dictated by American Heart Association (AHA) guidelines. For example, the PocketCPR application for iPhones and iPods may be used for practicing CPR, such as on a dummy or foam block, and may indicate whether a recent series of compressions was performed at the proper rate and proper depth. Similarly, the ZOLL Medical CPR D-Padz are defibrillation pads that connect to a defibrillator and include an accelerometer that can be used to compute the depth and rate of chest compressions on the victim so that the defibrillator can indicate via recorded voice prompts that a rescuer should be instructed, for example, to "press harder" if the unit determines that the depth of compression is too shallow.

Professional responders such as EMTs may also receive after-the-fact feedback via processes sometimes referred to as code reviews. In particular, data from a patient monitor (which may be incorporated into a defibrillator) may be saved and may then be loaded into a computer where the responder and a supervisor may review the data and then may discuss where the responder made errors or performed well, and what the responder can do to improve his or her performance. Sometimes these code reviews may occur well after the event, after the responder has largely forgotten the key aspects of the event.

SUMMARY

This document describes systems and techniques that may be used to gather information regarding the performance of CPR and other lifesaving techniques on a patient, and may provide one or more reports at a number of different locations for such performance. For example, data may be gathered for direct primary measurements of aspects of CPR, such as depth and frequency of compressions. That data may be reported immediately on a patient monitor while the rescuer is performing CPR. Additionally, derivative indicators of rescuer performance may also be determined for secondary indications of the performance of the CPR that are derived from two or more of the primary indicators. Such secondary indications may also be displayed to the rescuer while he or she is performing the CPR. In addition, while certain measurements may be reported for actions within a sub-set of a CPR cycle or interval, other measurements may be reported for a period across an entire interval, so that a rescuer can compare his or her current performance to performance for prior CPR intervals—where a CPR interval is the period for a complete cycle of monitoring, defibrillating, and providing a series of chest compressions to a patient, such as defined by the 2010 AHA CPR Guidelines.

Such information, and in particular the secondary derived information, may be used to generate a form of report card for the rescuer, where data for the report card may be displayed in real-time on a patient monitor along with the raw data (e.g., for rate and depth of compressions) used to generate the report card. As a result, the rescuer may receive greater motivation to improve his or her performance, given that he or she is being shown parameters on which his or her performance will ultimately be reviewed. The primary and secondary measurements may also be stored on the monitor and transferred off-site for further analysis. For example, other caregivers may receive the measurement data at substantially the same time it is being displayed to the rescuer. As one example, a team at an emergency room where the patient is to be taken may see the data either to provide direction to the rescuer or to identify opportunities to treat the victim while waiting for the victim to arrive at the emergency room.

Also, the primary and secondary measurements may be stored at a central system for later analysis and in-depth code reviews. For example, a particular rescuer may log into a patient monitor such as by typing a user name and password or by providing biometric identification (e.g., taking a digital picture of themselves or swiping a fingertip on an electronic fingerprint reader), and measurement data may subsequently be correlated to an identifier for the rescuer. When the data is provided to a central system, it may then be retrieved in combination with measurement data for other incidents with that rescuer by using the rescuer's identifier. Aggregate data across multiple rescue incidents may then be generated for a comprehensive code review, such as by determining the rescuer's perfusion level over multiple patients, so that the rescuer can determine that he or she needs to provide more complete perfusion, or to alter his or her performance in other helpful manners.

Such data may also be processed by a healthcare billing system so as to provide a check on a billing event submitted for a rescue event. In particular, the information may be used to verify a claim for payment made against the victim and by a caregiver organization. The content of the information may be reviewed to determine whether care was provided, and what care was provided, and may be checked against a formal claim for payment by the caregiver organization.

More general review of the data may also be performed across a larger rescuer population (i.e., across data for multiple different rescuers). For example, code reviews may be performed across rescuers in a single identified group—such as all rescuers who were trained in a particular class or program or all rescuers who are based out of a particular facility—to determine whether a particular endemic problem is manifesting itself in their rescue performance, and thus whether remedial action may be required with respect to each of the members in the group. Also, secondary data may be generated by a central system from the stored primary data, and may be compared to the secondary data that was generated by the patient monitors for particular incidents. For example, a company may identify new ways to measure a rescuer's performance and may test those new techniques against the manner in which the performance has been determined by monitors in the past, in order to determine whether the new techniques are an improvement over the old.

In certain implementations, the systems and techniques discussed here may provide one or more advantages. For example, by providing a rescuer with a real-time grade in the form of secondary, derived performance measurements that coincide with general measurements on which the rescuer will be evaluated, a system may provide greater motivation for the rescuer to improve his or her performance in real-time. Also, by showing primary real-time data next to data for prior CPR cycles, a rescuer can quickly determine whether current out-of-band performance is a temporary problem or has been a problem throughout a rescue incident. In addition, the rescuer can compensate for problems made in prior CPR cycles. The provision of such data to off-site locations can have further advantages, such as by allowing third parties (e.g., emergency room teams or post hoc evaluators) to have a better picture of the care that was provided to a victim. In addition, broader analysis of rescuer data may be performed, such as by researchers who may use the data to improve general procedures and guidelines for rescuers.

In one implementation, a computer-implemented method for providing summary information for lifesaving activities is described. The method comprises sensing one or more activities that are repeatedly and cyclically performed on a victim by a rescuer; identifying a cyclical timing interval over which performance is to be analyzed for a integer number of cycles of the one or more activities, and gathering data from the sensing of the one or more activities during the time interval; generating, from analysis of the one or more activities, summary data that condenses data sensed for the one or more activities into a summary of the one or more activities; and providing, for display to a user, a visual summary of the performance of the one or more activities over the identified time interval. The sensors can comprise one or more sensors selected from a group consisting of chest compression sensors, patient ventilation sensors, and electrocardiogram sensors. Also, providing the visual summary for display can comprise wirelessly transmitting data about the one or more activities from a device that senses the one or more activities to a remote device having a visual display device display. In addition, the remote device can be located in a rescue vehicle proximate to the device that senses the one or more activities. Furthermore, the device that senses the one or more activities can be wirelessly connected to the sensors, and the remote device can be located in a central medical facility that is distant from the device that senses the one or more activities, and data for generating the visual summary can be provided by transmission through a public data network.

In certain aspects, the summary comprises a score that indicates by one or more alpha-numeric indicators, a quality level with which the one or more activities were performed. In addition, the visual summary can be provided for display on multiple devices simultaneously. The method can also include monitoring electrocardiogram data of the victim while the one or more activities are occurring, and providing with a defibrillator at least one of charging the defibrillator and shocking the victim without manual intervention of a rescuer. In addition, generating summary data can comprise generating a single data value from information received from measurement of two or more distinct actions performed on the victim.

In another implementation, a system for providing summary information for lifesaving activities is disclosed that comprises a patient monitor having an interface for receiving signals from one or more patient-connected sensors; a rescuer performance analysis system programmed using stored instructions to incorporate data representative of a plurality of activities performed on a patient by a rescuer in the form of primary indications, and to generate secondary indications of the performance of cardiopulmonary resuscitation on the patient from the data; and one or more user interfaces to provide audible or visual indications of the generated secondary indications.

In yet another implementation, a computer-implemented system for providing summary information for lifesaving activities is disclosed. The system comprises a patient monitor having an interface for receiving signals from one or more patient-connected sensors; means for generating primary and secondary indications of cardiopulmonary resuscitation on a patent, the primary indications being direct representations of data measured from the patent, and the secondary indications being derived representations generated from one or more of the primary representations; and one or more user interfaces to provide audible or visual indications of the generated secondary indications.

The details of one or more embodiments are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

This detailed description discusses examples of implementations that may be employed in capturing data from a rescuer performing CPR and other related activities on a patient or victim (the terms are used interchangeably here to indicate a person who is the subject of intended or actual CPR and related treatment, or other medical treatment). The data may include both primary data that directly measures a parameter of an action performed on the patient, as well as secondary data that is derived from multiple pieces of the primary data. Also, the data may include real-time data for portions of a current CPR interval, and past data for prior CPR intervals. For example, a device may show the depth and rate of compression for the last compression (e.g., for depth) or last few chest compressions (e.g., for rate) performed by a rescuer. Adjacent that representation, the device may show the average rate and depth of compressions performed for each of the prior several CPR intervals. In such a manner, the rescuer can quickly see how they are doing and can adjust their performance accordingly, and then receive immediate feedback on whether their adjustments have been effective.

Figure 1A:
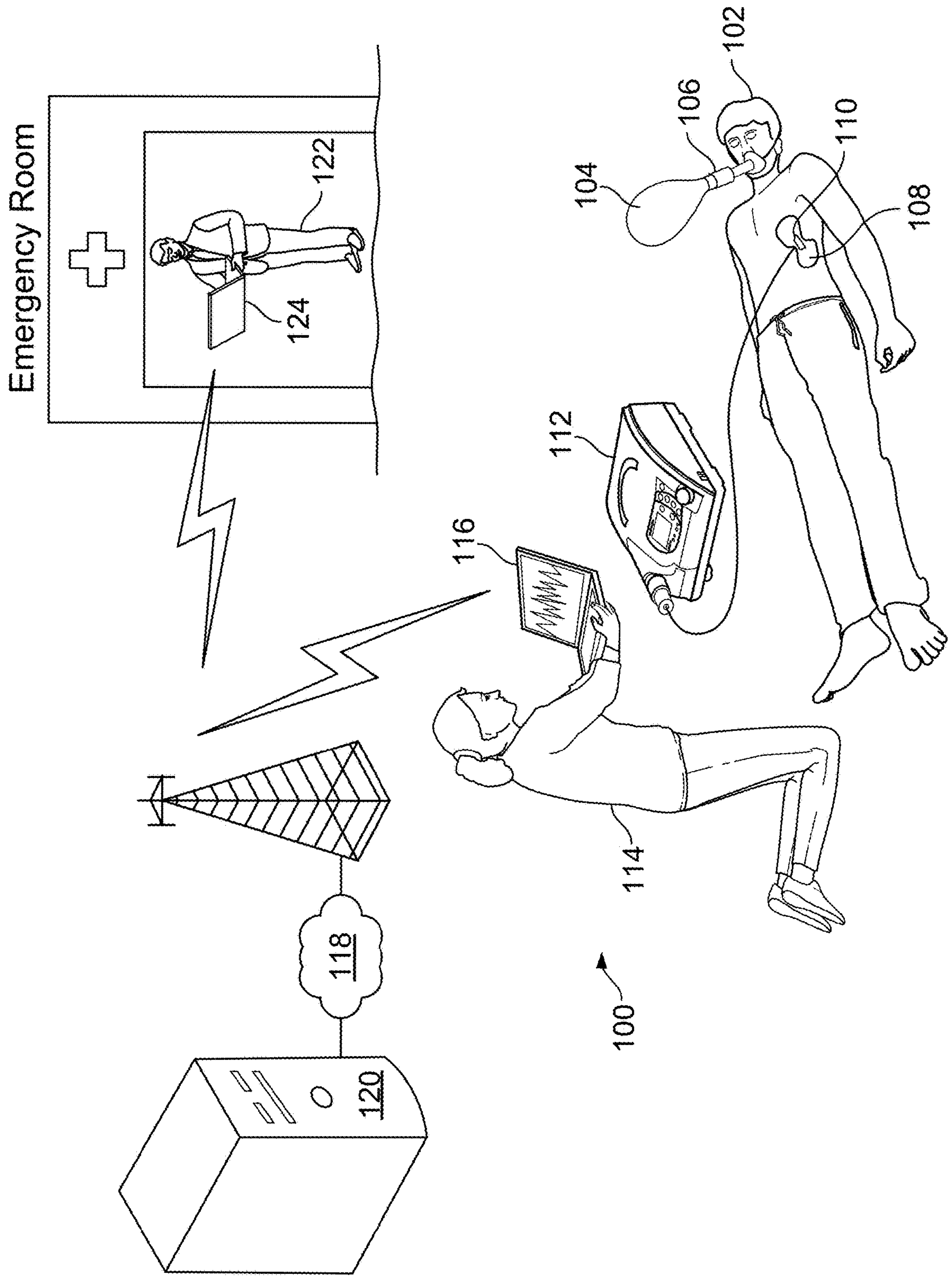
FIG. 1A shows a system for responding to an emergency medical condition.

FIG. 1 shows a system 100 for responding to an emergency medical condition of a victim 102. In general, system 100 includes various portable devices for monitoring on-site care given to a victim of an emergency situation, such as a victim 102 suffering from sudden cardiac arrest or a victim 102 at the scene of a traffic accident. The various devices may be provided by emergency medical technicians who arrive at the scene and who provide care for the victim 102, such as emergency medical technician 114. In this example, the emergency medical technician 114 has deployed several devices and is providing care to the victim 102. Although not shown, one or more other emergency medical technicians may be assisting and working in coordination with emergency medical technician 114 according to a defined protocol and training.

The emergency medical technician 114 in this example is interacting with a computing device in the form of a touchscreen tablet 116. The tablet 116 may include a graphical display by which to report information to the emergency medical technician 114, and may have an input mechanism such as a keyboard or a touchscreen by which the emergency medical technician 114 may enter data into the system 100. The tablet 116 may also include a wireless transceiver for communicating with a wireless network, such as a 3G or 4G chipset that permits long distance communication over cellular data networks, and further through the internet.

Separately, a portable defibrillator 112 is shown in a deployed state and is connected to the victim 102. In addition to providing defibrillation, the defibrillator 112 may serve as a patient monitor via a variety of sensors or sensor packages. For example, as shown here, electrodes 108 have been applied to the bare chest of the victim 102 and have been connected to the defibrillator 112, so that electrical shocking pulses may be provided to the electrodes in an effort to defibrillate the victim 102, and electrocardiogram (ECG) signals may be read from the victim 102. The defibrillator 112 may take a variety of forms, such as the ZOLL MEDICAL R Series, E Series, or M Series defibrillators.

The assembly for the electrodes 108 includes a center portion at which an accelerometer assembly 110 is mounted. The accelerometer assembly 110 may include a housing inside which is mounted an accelerometer sensor configuration. The accelerometer assembly 110 may be positioned in a location where a rescuer is to place the palms of their hands when performing cardio pulmonary resuscitation (CPR) chest compressions on the victim 102. As a result, the accelerometer assembly 110 may move with the victim's 102 chest and the rescuer's hands, and acceleration of such movement may be double-integrated to identify a vertical displacement of such motion (i.e., to compute the displacement of the victim's breastbone for comparison to American Heart Association (AHA) guidelines).

The defibrillator 112 may, in response to receiving such information from the accelerometer assembly 112, provide feedback in a conventional and known manner to a rescuer, such as emergency medical technician 114. For example, the defibrillator 112 may generate a metronome to pace such a user in providing chest compressions. In addition, or alternatively, the defibrillator 112 may provide verbal instructions to the rescuer, such as by telling the rescuer that they are providing compressions too quickly or too slowly, or are pushing too hard or too soft, so as to encourage the rescuer to change their technique to bring it more in line with proper protocol—where the proper protocol may be a protocol generated by the system, but that is inconsistent with any published protocols. In addition, similar feedback may be provided visually on a screen of the defibrillator, such as by showing a bar graph or number that indicates depth and another that indicates rate, with appropriate mechanisms to indicate whether the depth and rate or adequate, too low, or too high.

The defibrillator 112 may communicate through a short range wireless data connection with the tablet 116, such as using BLUETOOTH technology. The defibrillator 112 can provide to the tablet 116 status information, such as information received through the electrode assembly 108, including ECG information for the victim 102. Also, the defibrillator 112 can send information about the performance of chest compressions, such as depth and rate information for the chest compressions. The tablet 116 may display such information (and also other information, such as information from the defibrillator regarding $ETCO_2$ and $SPO_2$) graphically for the emergency medical technician 114, and may also receive inputs from the emergency medical technician 114 to control the operation of the various mechanisms at an emergency site. For example, the emergency medical technician 114 may use the tablet 116 to change the manner in which the defibrillator 112 operates, such as by changing a charging voltage for the defibrillator 112.

Where described below, the processing and display of data may occur on the defibrillator 112, the tablet 116, or on both. For example, the defibrillator 112 may include a display that matches that of the tablet 116, and the two may thus show matching data. In contrast, the defibrillator 112 may have a more limited display than does the tablet 116, and might show only basic information about the technician's performance, while the tablet 116 may show more complete information such as secondary historic information. Also, the processing of primary information to obtain secondary information may be performed by the defibrillator 112, the tablet 116, or a combination of the two, and the two devices may communicate back and forth in various manners to provide to each other information they have received or processed, or to relay commands provided to them by the technician 114.

Another electronic mechanism, in the form of a ventilation bag 104, is shown sealed around the mouth of the victim 102. The ventilation bag 104 may, for the most part, take a familiar form, and may include a flexible body structure that a rescuer may squeeze periodically to provide ventilation on the victim 102 when the victim 102 is not breathing sufficiently on his or her own.

Provided with the ventilation bag 104 is an airflow sensor 106. The airflow sensor 106 is located in a neck of the ventilation bag 104 near the mouthpiece or mask of the ventilation bag 104. The airflow sensor 106 may be configured to monitor the flow of air into and out of the patient's mouth, so as to identify a rate at which ventilation is occurring with the victim. In addition, in certain implementations, the airflow sensor 106 may be arranged to monitor a volume of airflow into and out of the victim 102.

In this example, the airflow sensor 106 is joined to a short-range wireless data transmitter or transceiver, such as a mechanism communicating via BLUETOOTH technology. As such, the airflow sensor 106 may communicate with the tablet 116 in a manner similar to the communication of the defibrillator 112 with the tablet 116. For example, the airflow sensor 106 may report information that enables the computation of a rate of ventilation, and in some circumstances a volume of ventilation, that is being provided to the patient. The tablet 116, for example, may determine an appropriate provision of ventilation and compare it to the level of ventilation that the victim is receiving, and may provide feedback for a rescuer, either directly such as by showing the feedback on a screen of the tablet 116 or playing the feedback through an audio system of the tablet 116, or indirectly, by causing defibrillator 112 or airflow sensor 106 to provide such feedback. For example, defibrillator 112 or airflow sensor 106 may provide a metronome or verbal feedback telling a rescuer to squeeze the ventilation bag 104 harder or softer, or faster or slower. Also, the system 100 may provide the rescuer was an audible cue each time that the bag is to be squeezed and ventilation is to be provided to the victim 102.

Such feedback may occur in a variety of manners. For example, the feedback may be played on built-in loudspeakers mounted in any of tablet 116, defibrillator 112, or airflow sensor 106. Alternatively, or in addition, visual notifications may be provided on any combination of such units. Also, feedback may be provided to wireless headsets (or other form of personal device, such as a smartphone or similar device that each rescuer may use to obtain information and to enter data, and which may communicate wirelessly over a general network (e.g., WiFi or 3G/4G) or a small area network (e.g., BLUETOOTH) that are worn by each rescuer, and two channels of communication may be maintained, so that each rescuer receives instructions specific to their role, where one may have a role of operating the defibrillator 112, and the other may have the role of operating the ventilation bag 104. In this manner, the two rescuers may avoid being accidentally prompted, distracted, or confused by instructions that are not relevant to them.

A central server system 120 may communicate with the tablet 116 or other devices at the rescue scene over a wireless network and a network 118, which may include portions of the Internet (where data may be appropriately encrypted to protect privacy). The central server system 120 may be part of a larger system for a healthcare organization in which medical records are kept for various patients in the system. Information about the victim 102 may then be associated with an identification number or other identifier, and stored by the central server system 120 for later access. Where an identity of the victim 102 can be determined, the information may be stored with a pre-existing electronic medical record (EMR) for that victim 102. When the identity of the victim 102 cannot be determined, the information may be stored with a temporary identification number or identifier, which may be tied in the system to the particular rescue crew so that it may be conveniently located by other users of the system.

Information that is stored for a rescue incident may also include an identifier for the technician 114 and any other technician that participated in the rescue. Using such identifiers, the server system 120 may later be queried so as to deliver data for all incidents that the particular technicians have been involved in. The tablet 116 or defibrillator 114 may include mechanisms so that the technicians can identify themselves and thus have their identifier stored with the information. For example, the technicians may be required to log in with the tablet 116 when their shift starts, so that all information subsequently obtained by the tablet 116 or components in communication with the tablet may be correlated to the identifier. Such logging in may require the entry of a user name and password, or may involve biometric identification, such as by the pressing or swiping of a technician's fingertip on a fingerprint reader that is built into the tablet 116.

The information that is stored may be relevant information needed to determine the current status of the victim 102 and the care that has been provided to the victim 102 up to a certain point in time. For example, vital signs of the victim 102 may be constantly updated at the central server system 120 as additional information is received from the tablet 116 (e.g., via the defibrillator 114). Also, ECG data for the victim 102 may be uploaded to the central server system 120. Moreover, information about drugs provided to the victim may be stored. In addition, information from a dispatch center may also be stored on the central server system 120 and accessed by various users such as rescuers. For example, a time at which a call came in may be stored, and rescuers (either manually or automatically through their portable computing devices) can use that time to determine a protocol for treating the patient (e.g., ventilation or chest compression needs may change depending on how long the victim has been in need of treatment).

Other users may then access the data in the central server system 120. For example, as shown here, an emergency room physician 122 is operating his or her own tablet 124 that communicates wirelessly, such as over a cellular data network. The physician 122 may have been notified that victim 102 will be arriving at the emergency room, and, in preparation, may be getting up-to-speed regarding the condition of the victim 102, and determining a best course of action to take as soon as the victim 102 arrives at the emergency room. As such, the physician 122 may review the data from central server system 120. In addition, the physician 122 may communicate by text, verbally, or in other manners with emergency medical technician 114. In doing so, the physician 122 may ask questions of the emergency medical technician 114 so that the physician 122 is better prepared when the victim 102 arrives at the emergency room. The physician 122 may also provide input to the emergency medical technician 114, such as by describing care that the emergency medical technician 114 should provide to the victim 102, such as in an ambulance on the way to the emergency room, so that emergency room personnel do not have to spend time performing such actions. Also, physicians could see aspects of a currently-operating protocol on the system (e.g., an AHA CPR protocol), and could act to override the protocol, with or without the rescuers needing to know that such a change in the protocol has been made (e.g., their devices will just start instructing them according to the parameters for the manually-revised protocol).

Where the published protocol is organized in a flowchart form, the flowchart may be displayed to a rescuer or a physician, and such user may drag portions of the flowchart to reorder the protocol. Alternatively, the user could tap a block in the flowchart in order to have parameters for that block displayed, so that the user can change such parameters (e.g., ventilation volume or time between ventilations). Data describing such an edited protocol may then be saved with other information about an incident so that later users may review it, and a user may save reordered protocols so that they can be employed more easily and quickly in the future.

In this manner, the system 100 permits various portable electronic devices to communicate with each other so as to coordinate care that is provided to a victim 102. In addition, the system 100 allows the technician 114 and others to see raw real-time data and derived real-time or historical data about a rescue attempt. Such data may be arranged so that a technician can immediately see whether his or her performance is matching or has matched agreed-upon standard, and can quickly adjust his or her performance while the incident is still going on. In addition, such information may be aggregated across multiple incidents for a particular rescuer, and across multiple incidents for multiple rescuers so as to be able to provide more broad-based report cards for performance, and to permit more general modification of future performance (e.g., for a rescuer who regularly underperfuses victims).

Each device in the system 100 may sense information about the care provided to the victim 102, and/or may provide instructions or may store data about such care. As a result, the system 100 may provide improved care for the victim 102 by better integrating and coordinating each form of the care that the victim 102 receives. The victim 102 made thus receive improved care and an improved chance of obtaining a positive outcome from an event.

In certain instances, a condition of a victim that is used to generate a protocol for treatment of the victim may be based on on-site observations made by a rescuer, by information in an EMR for the victim, or both. For example, a determination from an EMR that a victim is taking a particular drug may result in a change in protocol for ventilation rate. Likewise, an observation by a rescuer that the victim has suffered a head injury on site may also affect the protocol for ventilation rate. The two factors may also be considered together to determine yet a more refined ventilation rate for which a rescuer will be instructed to provide to the victim. Also, the real-time feedback that is provided to a technician 114 may be automatically altered in response to identifying such special cases in an EMR or in information entered by the technician 114 (e.g., after a conscious victim has provided the information to the technician 114).

Thus, in operation, a two-person rescue team may arrive at a scene. One member of the team may set up and attach a defibrillator/monitor to a victim, and do the same with a ventilation bag assembly. The other member may begin an examination of the victim and may enter information obtained from the examination into a portable computing device such as a general tablet computer (e.g., an iPad or netbook). In some situations, the second rescuer may be able to verbally interview the victim, at least initially, so as to determine whether the victim is lucid, what drugs the victim may be taking, and the like. The second rescuer could also make visual observations (e.g., types of trauma to the victim) and record those in the computing device. Moreover, one of the rescuers may obtain vital sign information for the victim, and such information may be entered manually into the computing device or automatically, such as through wireless links from a blood pressure cuff, or other relevant medical device.

The computing device, using all of the entered information, may then generate a protocol for treating the victim. Such a generating may occur by selecting from among a plurality of available protocols by plugging the observations into a protocol selector. The generation may also be more dynamic, and may depends on a series of heuristics that use the observations as inputs, and generate a protocol (which may be made up of one or more sub-protocols) as an output. Moreover, a lookup table may be consulted, where the table may define correlations between particular observed patient conditions or physical parameters, and a particular feature of a treatment protocol.

The computing device may also submit the observation information over a network such as the internet, and a protocol may be generated by a central computer server system and then automatically downloaded to, and implemented by, the portable computing device. Such an approach may have the benefit of being able to easily update and modify protocol-generation rules.

The computing device may then receive information about the performance by the rescuers, such as from wired or wireless transmitters on a defibrillator, an assisted ventilation unit, or other medical device (e.g., blood pressure reader). The computing device may provide feedback or coaching when the performance falls out of line with a defined protocol, or may provide feedback to maintain the performance in line with the protocol. In providing the feedback, the computing device or the defibrillator/monitor may generate a number of derived parameters from measure parameters of the victim, and both the measured parameters and the more comprehensive derived parameters may be reported visually or audibly by the computing device, the defibrillator/monitor, or both. Also, the computing device may update the protocol as care is being provided to the victim. For example, the rate of required ventilation or chest compressions may change as a function of time. Also, if one of the rescuers attaches an oxygen source to a ventilation assembly (as sensed, e.g., by a switch where the connection occurs, by a manual rescuer input to the system, or by sensors in the assisted ventilation system), the rate of required ventilation may change. Other changes in the patient condition, such as changes in measured levels of $ETCO_2$ or $SpO_2$, can lead to the computing device generating a revised protocol and providing feedback to the rescuers so that they adapt to the revised protocol (sometimes without consciously knowing that the protocol has been revised).

Figure 1B:
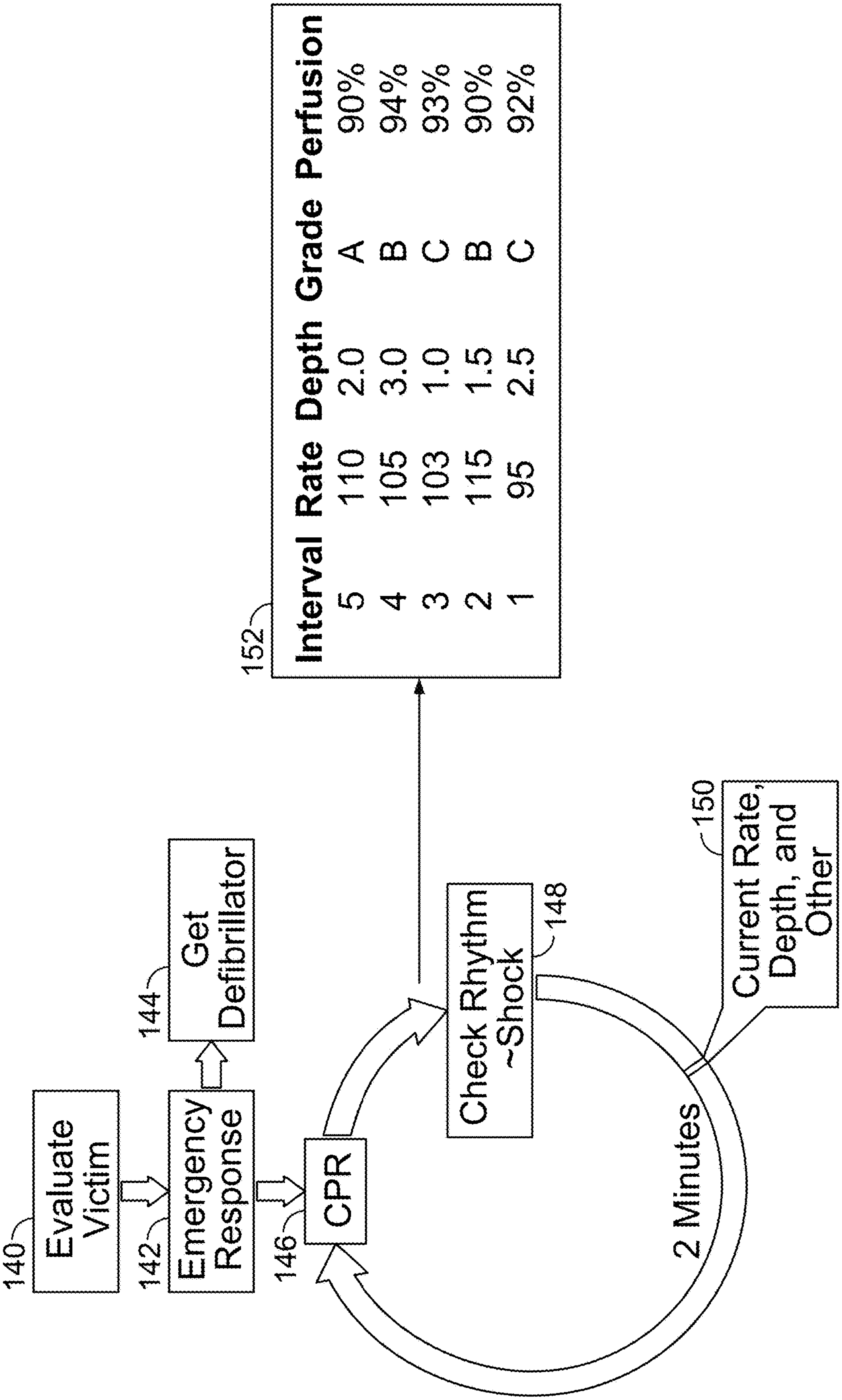
FIG. 1B is a flow diagram of a CPR data acquisition process.

FIG. 1B is a flow diagram of a CPR data acquisition process. In general, the data acquisition occurs in parallel with performance of CPR according to the 2010 American Heart Association Guidelines for Cardiopulmonary Resuscitation and Emergency Cardiovascular Care. Data acquisition in this example occurs in real-time throughout the provision of CPR to a victim, and such real-time data may be continuously updated and displayed to rescuers or others. Also, certain secondary information may be generated from the real-time information, either periodically such as at the end of each CPR interval in the cycles, or at the end of a rescue incident (where an incident is an entire attempt to rescue a victim, from the beginning of data collection to the time a patient monitor is removed from a patient, the patient leaves the scene of the incident, or another rescuer or group of rescuers takes over).

According to the CPR guidelines, the process begins at box 140, where a rescuer endeavors to evaluate a victim. Such evaluation may occur by familiar mechanisms, such as by determining whether the victim is breathing, responsive, or has a pulse. If a problem with the victim is determined, the rescuer begins an emergency response at box 142. For example, the rescuer may cause an emergency response team to be called to the scene and may get a defibrillator 144 or cause another person to get a defibrillator if the victim appears to suffer from sudden cardiac arrest or a similar problem.

Having performed such actions, the rescuer may begin performing cardio pulmonary resuscitation (CPR) on the victim at box 146. According to protocol, CPR involves a cyclical process that is repeated every two minutes, as indicated by the circular arrow in the figure. At the beginning of each cycle, a defibrillator that has had leads attached to the victim may analyze the victim, such as by analyzing an ECG reading for the victim or other information to determine whether the victim has a shockable rhythm. Techniques for performing such analysis are well-known and the particular technique that is used here is not critical. If a shockable rhythm is determined to be present, a shock may be delivered as shown by box 148. For example, the defibrillator may provide a display to a rescuer or may speak words to the rescuer indicating that a shock should be delivered. The rescuer may then press a button on the defibrillator to cause a shock to be delivered, after all people around the victim have moved away from the victim.

The rescuer may then perform chest compressions on the victim for the remainder of the cycle or interval. After a predetermined time period of providing chest compressions, or during the chest compressions, the defibrillator may again analyze the victim's condition to determine whether they have a shockable rhythm. For example, the defibrillator may include componentry for filtering out CPR artifacts from chest compressions as compared to an ECG signal, and may perform the analysis on the filtered signal.

Box 150 is shown along the loop of the CPR cycle to indicate a current time in the cycle. In particular, the box 150 indicates that the defibrillator or another device may, at the current point in time, be computing and displaying certain parameters regarding the care that is being provided to the victim. Certain of those parameters may be initial or primary parameters in that they are direct representations of values read from the patient. Such parameters may include depth and rate of chest compressions provided to the victim. Other of the reported parameters may be secondary parameters in that they are derived from the initial parameters, either from one or a multiple of different initial parameters. For example, certain values may be computed from a combination of the compression rate and the compression depth. Also more general composite values may be generated, such as a letter or number grade that indicates how the rescuer is currently performing.

Box 152 represents values that are generated periodically, such as with each cycle of a CPR interval in a particular location in the interval, or at the end of an incident. The values that are generated may include, for example, average values for particular primary parameters over a period of an interval. For example, the average rate and depth over an interval may be computed at the end of each interval and may be saved in a database such as in a manner shown by box 152. Also, the saved parameters may include derived or secondary parameters that are computed from initial parameters, such as from average values of initial parameters, or by combining multiple initial parameters from throughout an interval, and then averaging the combination. In this example, a profusion percentage is given as one example of a secondary or derived parameter, and letter grades for each interval are also secondary or derived parameters.

In this manner, a performance reporting approach may be implemented in coordination with standard CPR techniques so as to capture and report information that is particularly relevant to a rescuer or to a party after the fact of a rescue. The information may include basic measurements from the performance of CPR on a patient, and may also include derived values that may provide a model or compelling or understandable representation of the rescuers performance. For example, the parameter that is displayed to the rescuer may be similar to or the same as a parameter on which the rescuers performance will be judged by a later review work of an incident as part of the code review. The rescuer may thus be more responsive to such a displayed parameter if the rescuer is performing poorly, than the rescuer would be in response to simple values of depth and rate of compressions. As a result, the rescuer may be more likely to change his or her behavior in a positive manner so as to improve the care that is provided to a patient or victim.

The monitoring and feedback provided by such a process may also be affected by basic configuration data obtained by the system. For example, before monitoring by the system begins, a process may have gathered certain data to aid in the monitoring. For example, as a rescuer sets up a defibrillator and hooks it to a victim, the defibrillator may ask the rescuer (on a display or via a spoken request) whether the rescuer is alone or is being aided, and might also ask how many additional rescuers are available. If the rescuer indicates that he or she is alone, then the system may follow a branch of programming that does not recommend switching of rescuers, but might more aggressively provide feedback in order to overcome the extra fatigue a solo rescuer will face. If the rescuer is accompanied, then the system may subsequently indicate when rescuers are to switch roles. The system may also assign a label to each rescuer, such as "Rescuer 1" and "Rescuer 2" or the actual names of the rescuers (which could have been programmed previously, such as for EMTs who use the system frequently, or could be obtained, such as by lay rescuers speaking their names into the device in response to prompts from the device). If there are three or more rescuers, instructions for rotating may be more complex—i.e., involving more than simply an instruction to switch positions, but instead telling each rescuer what component of CPR they should be performing for any particular time period.

A determination about the number of rescuers may also be made inferentially. For example, a ventilation bag may include electronics that report to a defibrillator or other box, and the box may sense that the bag is being deployed or used, or is being used simultaneous with chest compressions being performed, in order to infer that there are at least two rescuers. The defibrillator may adjust its operation accordingly in the manners discussed above in such a situation (e.g. by enabling prompts for rescuers to switch roles).

As for operation of the system during performance of CPR, in certain circumstances, prompts for performing CPR may change the way in which CPR is to be performed in response to indications that there has been a degradation in performance. For example, a protocol by which a user is instructed may change based on such an observation that performance has degraded, so as hit a performance level that the user can better maintain, even if that level is sub-optimal. In particular, prompting of CPR at a sub-optimal level may be provided, as long as that sub-optimal level is better than wholly fatiguing a rescuer.

For example, hemodynamics data has indicated that depth of chest compressions may be more important to victim well-being than is rate of compressions—i.e., it may essentially not matter how fast you are performing compressions if none of those compressions is truly effective. As a result, a system may slow a rate (e.g., a metronome) of prompting compressions and may monitor how the depth of compressions changes in response to the prompted change in rate. Using stored hemodynamic data correlating depths and rates to effectiveness, the system may identify a most-preferred rate that maximizes the hemodynamic effect for a particular rescuer (using, e.g., the well-known Windkessel model or other approach). While such modifications may be made only after sensing that a particular rescuer is fatiguing, they can also be initiated at other points and in response to other criteria, including by making such adjustments throughout a rescue cycle (e.g., the rate of a metronome may be adjusted slightly and essentially continuously, and the combination of depth and rate that is measured from the rescuer may be input in real-time to a formula for computing hemodynamic effect, with subsequent changes in the rate of the metronome being made in an attempt to increase the hemodynamic effect within bounds of safety).

Also, physical data of the rescuer or rescuers may also be monitored while care is being provided to a victim, such as to determine whether the rescuers are tiring and should be prompted in a different manner, or should be instructed to switch out to other rescuers as they fatigue. For example, a rescuer may be outfitted with a pulse oximeter such as one that can be attached to a CPR puck on a victim's chest and into which the rescuer can place one or more fingers. The readings of the rescuer's blood oxygen level and pulse rate may be used to determine that the rescuer is fatiguing and will not be able to continue performance at a current level for very long. As a result, a medical device can cause the rescuer to switch places with another rescuer, may provide encouragement to the rescuer, or may reduce the rate or severity with which the rescuer is providing care so as to maximize the work the rescuer can do, even if it is below what would otherwise be considered an optimum level of care.

Thus, these techniques may be used to identify rescuer performance, including indications of fatigue while providing such performance, for review by the rescuers or other at various points in time. For example, a medical device may immediately monitor the performance to provide feedback or adjust the manner in which it provides feedback so as to maintain a best level of performance over the length of a rescue operation, including by instructing rescuers to switch places at appropriate times so as to lessen the effect of fatigue. The rescuers themselves may also be provided with information as described above and below so that they may adjust their performance of care on a victim in real-time as they perform the care. Also, care may be reviewed after the fact, such as by rescuers to determine how they can perform better as a team or perhaps to determine that they should increase their physical conditioning to combat fatigue, and also by supervisors.

Figure 2A:
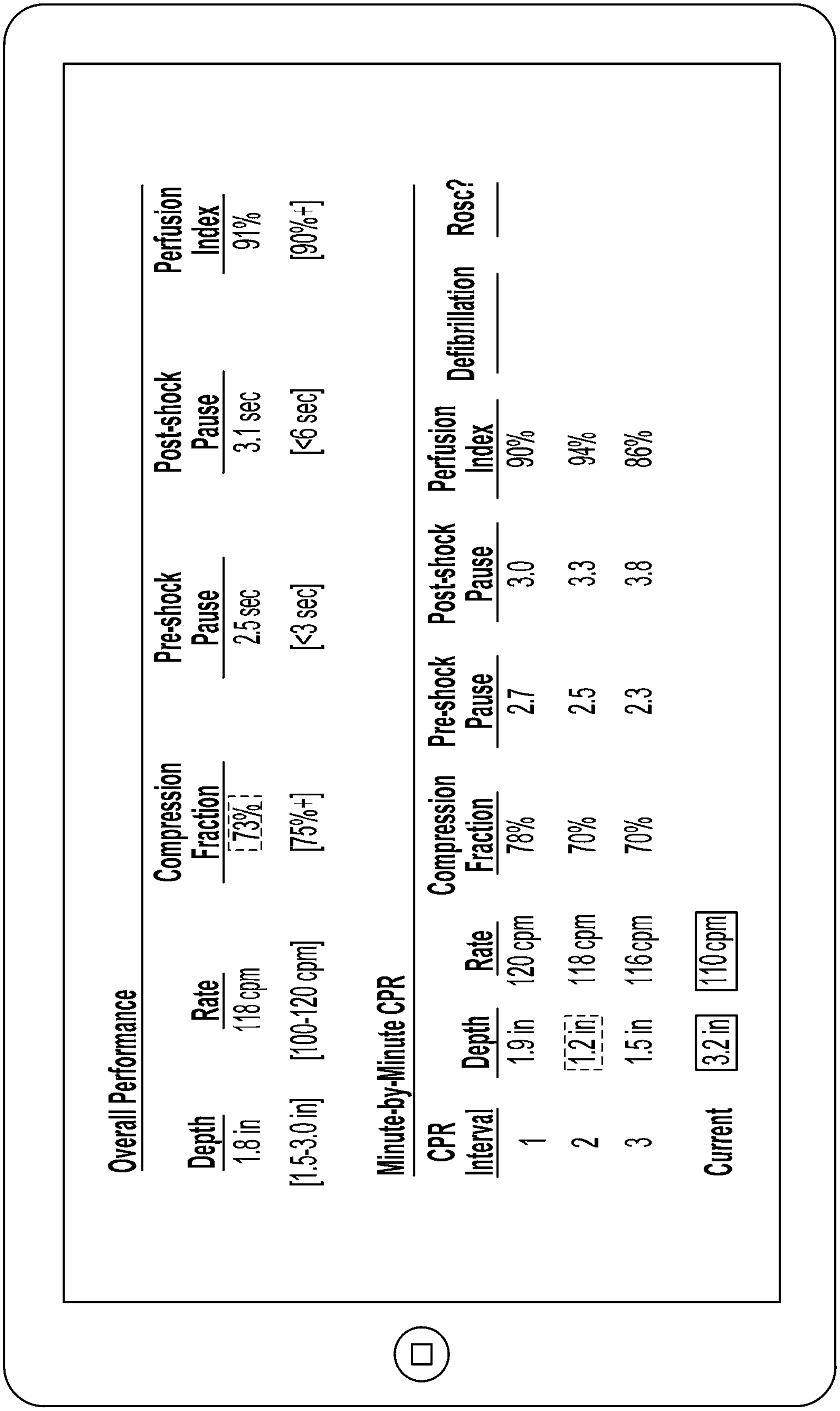
FIGS. 2A and 2B are screen shots of a tablet device showing a summary of rescuer performance in a CPR setting.

FIG. 2A is a screen shot of a tablet device showing a summary of rescuer performance in a CPR setting. In general, the screen shot shows roughly the sort of parameters that may be displayed on a tablet computer as feedback for a rescuer at the scene of an accident, or to a physician who is following the performance of care on a victim remotely.

The presentation of information in this example is split into two portions—a top portion that shows averaged performance over an entire incident, and a bottom portion that shows the performance average over each of the last three CPR intervals, with display of current depth and rate displayed immediately under the second portion.

Referring now to particular portions of the display, a rescuer is shown that their average depth of compression in performing CPR has been 1.8 inches for an incident, and that the appropriate range for compression is 1.5 inches to 3.0 inches. Similarly, the rescuer is shown that their average rate of compressions is 118 compressions per minute (CPM), which is within the approved range of 100 to 120 CPM. The approved range for compression fraction is over 75%, but the average for this rescuer is 73%. The fact that the rescuer is outside of the approved range is indicated here by a dashed box around the average value, to draw attention of the rescuer to the fact that improvement is needed in this value. Similarly, values are displayed for the rescuer's delay in pre-shock and post-shock activity and for a profusion index by the rescuer. The particular values shown here were selected merely to demonstrate how values may be displayed to a rescuer, such as on a defibrillator/monitor, tablet computer, or similar device, and are not meant to represent actual values that would necessarily be displayed in an actual situation.

In the minute-by-minute CPR area of the display, three lines of values are shown, where the values are average values for each of the last three CPR intervals performed on the victim, so they represent approximately the last six minutes of CPR performed on the victim, though perhaps not the entirety of CPR that has been performed on the victim. Again, individual values are provided for each of the intervals, and values that are outside of range are highlighted by a dashed box, though as discussed below, other mechanisms for drawing attention to out-of-range or in-range values may be employed.

Also, two of the values—for depth and rate of compression—are shown according to their current states. Specifically, the last compression performed by the rescuer had 3.2 inches of travel, and the last several compressions were performed at a rate of 110 CPM. Solid boxes are shown around these values to draw particular attention to them for the rescuer, so that the rescuer can quickly see what his or her immediately current performance has been.

Additional guidance may be provided to a viewer of the display, such as to a rescuer, by using color, animation, and sound feedback. For example, any values on the display that are outside a desired range may be displayed in red, while values at the edge of the range may be displayed in yellow, and values inside the range may be displayed in green color. Also, particularly important values may be highlighted by making them blink, wiggle, or shimmer, so as to call a viewer's attention particularly to them. Also, the device may beep or speak recorded instructions when the rescuer needs guidance in returning to approved performance ranges.

The particular arrangement of values on the display here is provided merely as an example of data that may be shown to a rescuer or to a physician while care is being provided to a victim. Other arrangements of information may also be employed. In particular, less information than is shown here may be provided, and may be shown in a smaller portion of the screen, thus leaving room for the display of other information that may be pertinent to a rescuer. One such example is shown in FIG. 2B.

Figure 2B:
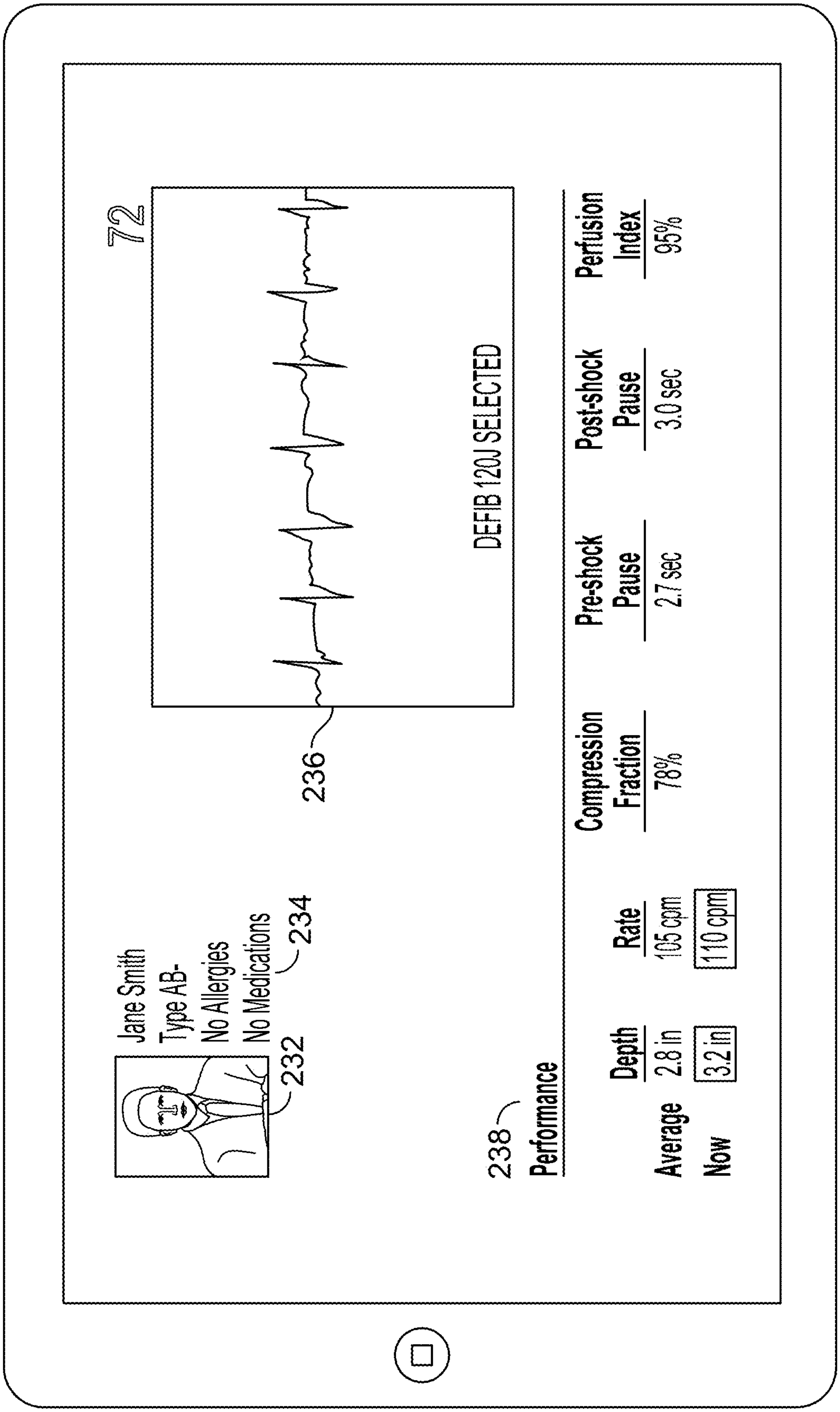

In particular, FIG. 2B shows another screen from a device such as a patient monitor or tablet computer that may be displayed to a rescuer. In this example, a performance area 238 (i.e., an area that rates and reports on the rescuer's performance) takes up a relatively small part of the entire display. The data that is displayed is similar to that displayed in FIG. 2A, but only average values across the entire incident, and immediate values for depth and rate, are displayed. A numerical or alphabetical grade (not shown) may also be provided near this area as a higher level, more summarized, view of the performance.

The relatively small size of the performance area 238 leaves additional room on the display to show other data about a rescue incident. For example, a victim identification area in the upper left corner of the display includes an image 232 of the victim and personal information 234 about the victim. The image 232 may be obtained from a central server system in response to entering identification information for the victim. For example, a driver's license found with the victim may indicate a name of the victim, or a fingerprint may be obtained from a fingerprint reader for the victim, where the fingerprint reader may be incorporated with a blood oxygenation sensor. Such a mechanism for identifying the victim may be used to recover limited medical record information about the victim, such as the blood type, allergies and medications taken by the victim. The image 232 may be displayed so that the rescuer may manually confirm that the patient who is identified by the system is the same person as the victim who is lying front of them (where the victim is unable to identify himself or herself).

An ECG display 236 is also provided in a familiar manner in an area the display 236, showing an ECG trace and may also display warnings or other data such as an indication of the amount to which capacitors on a defibrillator have been charged, and whether they are ready for discharge. Other information that is not shown here may also be provided on the display. For example, countdown timers may be shown to indicate future activities that will need to be performed by the rescue team. As one example, a countdown timer may indicate the amount of time left in a CPR interval. Also a countdown timer may indicate time for a another rescuer, such as time for providing ventilation to the patient or victim, or time until a particular drug is to be provided by the rescuers to the victim.

The display may also show content that is typed by a physician at an emergency room, or other similar content. For example, the physician may monitor information like that shown in this figure, and may provide guidance to a rescuer by typing it, similar to an online chat system. In other implementations, a voice connection may be made up with the physician, and instructions from the physician may be heard through the tablet computer, the defibrillator monitor, a BLUETOOTH headset that is provided with data from the tablet or monitor, or through another form of communication device employed by the rescuer.

Using displays like those shown in FIGS. 2A and 2B, a system may provide improved feedback to a rescuer in an emergency situation. The feedback may be provided in a graphical manner that indicates information that is most important to the rescuer, and is thus most likely to be acted upon by a rescuer. Also, the information that is provided may be a form of combined information that provides a higher level view of the rescue operation. For example, a number of different actions or activities that are performed by a rescuer on a victim may be combined using a predetermined formula or algorithm to produce a more general descriptor of the quality of care that is given to the victim. Such automatic combination by the system may relieve a rescuer of having to make such determinations themselves. For example, a particular combination of compression rate and depth, albeit nominally out of range for either rate or depth or both, may be within a desired range when the values for rate and depth are applied against each other, such that out of range values for each variable cancel each other out. Also, where the information is more generalized, it may be more in line with the form of information on which the rescuer will be judged in the performance of their job, so that a rescuer may be more likely to respond to it.

Figure 3:
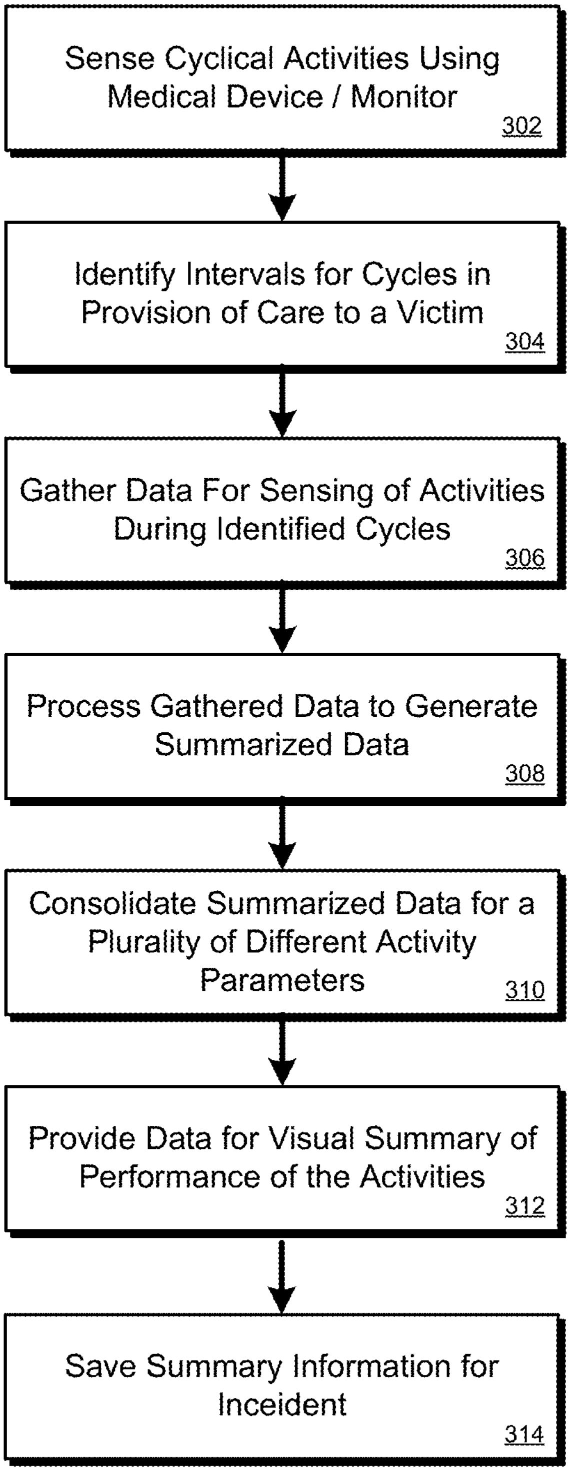
FIG. 3 is a flow chart of a process for capturing user performance data during the provision of CPR.

FIG. 3 is a flow chart of a process for capturing user performance data during the provision of CPR. In general, the process involves receiving raw information from sensors that are connected to a patient monitor, which may be incorporated into a defibrillator as described above, generating derivative data, displaying to a user of the monitor values for the raw data and the derivative data, and also displaying values for real-time measurements and historic measurements. For example, the real-time raw measurements may include depth and rate of compression during CPR that is being performed on a patient who is being monitored. The derived measurements may include a perfusion percentage and overall letter or number grade for the performance of the user. The historical measurements may include measurements for portions of, or all of, prior CPR intervals, or for averages from such periods or across multiple intervals.

The process begins at box 302, where a medical device/monitor, such as a defibrillator with built-in capabilities for monitoring motion of chest compressions and ECG signals, among other parameters, senses cyclical activities that are being performed on a patient. Such cyclical activities may include the provision of CPR in a recursive cycle following the 8H a guidelines discussed above, where the cycle involves analyzing a patient such as to determine whether the patient exhibits a shock of all heart rhythm, providing a shock if the patient has such a rhythm, and providing chest compressions to the heart to cause perfusion of blood in and through the heart. The particular activities may generate data from sensors, and the step of sensing the activities may include converting the data to a more usable form, such as by converting a voltage received from an accelerometer into a computed depth of compression for a patient's chest.

At box 304, the process identifies intervals for the cycles in the provision of care to the victim or patient. Thus, for example, the process may identify starting and ending points for each of the CPR intervals and may thereby associate data received between each start point and end point with a particular one of the intervals. Such association of received data with particular intervals may enable the presentation of information about the data to a user in a manner that the information is correlated to the particular intervals in which it was received.

At box 306, data is gathered for sensing activities during the identified cycles. Such data gathering may be continuous during the performance of CPR and other activities on a patient or victim, such that particular ones of the actions described here may be repeated over and over until a rescuer terminates a monitoring described here. As the data is gathered, it may receive a first level processing, such as described above to convert voltages into more usable values such as displacements or accelerations. Similarly, the monitor may change voltages from leads that are attached to the patient into values for an ECG signal that may be easily graphed on the monitor or on another device. Such initially-processed data may then be stored on the device, and copies of some or all of the data may be provided to other devices. For example, the data may be transferred over a short range wireless connection to a device such as a tablet 116 or server 120 in FIG. 1. Such transfer of data may be in batches or may be continuous or substantially continuous. For example, an automatic batch upload of data may be triggered at particular points during treatment of a patient, such as after a rescuer terminates treatment. A proximity sensor may be used to determine that pretreatment has terminated because the monitor has returned to a vehicle such as ambulance, and such sensing may be used to trigger the batch transfer of data between the monitor and devices in the ambulance, and then further to a separate device such as server 120. In another implementation, the batch transfer may be triggered by a GPS unit in the device sensing that the device is moving above a particular speed, such as 15 mph, and thus concluding that the device has been placed in an ambulance and that its use is complete. Such determination may also be combined with a determination that patient conditions are no longer being received from the various sensors to which the device has been connected. Continuous transfer of data may occurred by a variety of mechanisms, such as by caching received and initially-processed data, and then uploading or otherwise transferring the data at close-spaced periods.

At box 308, the gathered data is processed to generate summarized data, which is a derivative form of the initially gathered data. For example, information about rate and depth of chest compressions may be used along with other information obtained by a system to identify a level of perfusion for a patient. In addition, summaries may be generated for entire CPR intervals or multiple CPR intervals. As one example, particular values that have been captured and recorded for performance of activities on a patient may be aggregated, such as by generating an average value for a CPR interval or an average value across multiple CPR intervals. Thus, for example, a perfusion level for the entire time that a rescuer has been performing CPR on a patient may be computed and may be reported back out to the rescuer.

Also, as shown at box 310, summarized data may be consolidated across a number of activities, such as data relating to chest compressions and data relating to ventilation that can be combined to identify an overall indicator of care that is been provided to the patient. Thus, in such examples, the derivative data may not only be derived from the original data, such as depth of compression, but may also be derived from two separately obtained pieces of original data. Such combining of data sources across multiple activities being performed on the patient may also be used to generate a score or grade for the care provided so far to the patient, so as to indicate manners in which the rescuer can change subsequent care that is given. For example, monitoring of parameters like those discussed in FIGS. 2A and 2B may indicate that a rescuer is too excited or too relaxed in giving their care (e.g., because they are compressing the chest too soft or too hard, or they are acting too quickly or too slowly in certain parts of the CPR interval). In such a situation, a score from −5 to +5 may be assigned, where a score of 0 is perfect, scores farther below 0 indicate that the rescuer needs to be more active in their care, and scores above 0 indicate that the rescuer needs to take a deep breath and relax a bit. Such a score may be displayed in a location on a screen of a monitor, tablet computer or similar computing device. The score or grade for the entire session may also be submitted to a supervisor of the rescuer as part of a post hoc code review of the session.

Such presentation of the raw and derived data is represented by box 312, where a visual summary of the user's performance is displayed. Such display, as discussed above, can be on a monitor, on a tablet, on a separate computer used by another caregiver, or by other mechanisms. The display may take a form, for example, similar to that shown in FIGS. 2A and 2B.

At box 314, summary information for an incident or session is saved. Such a step could take place continuously or semi-continuously throughout an incident or may occur as a batch upload once the incident is over, as discussed above. The information may be saved locally and may also be saved on a more global server system from which supervisors or analysts may access both the raw and derived data. Presentations of the data similar to those shown above may be provided, and a replay may be had of the data that would have been displayed to the rescuer. As a result, the rescuer and an official may step through the session step-by-step, and the official may point out exactly what the rescuer did right and wrong. The presentation may also take a more summarized form, and can roll in data from multiple different incidents, such as all recent incidents of a particular type for a particular rescuer (e.g., all incidents in which a victim suffered a severe sudden cardiac arrest or similar trauma). For example, using the −5 to +5 scoring technique described above, a supervisor may be presented with scores for a dozen recent incidents for a rescuer, and may notice that the scores are generally below 0. The supervisor may then determine to provide the rescuer with training in being more aggressive (i.e., providing harder chest compressions, and reacting more quickly to prompts during a CPR interval).

Figure 4:
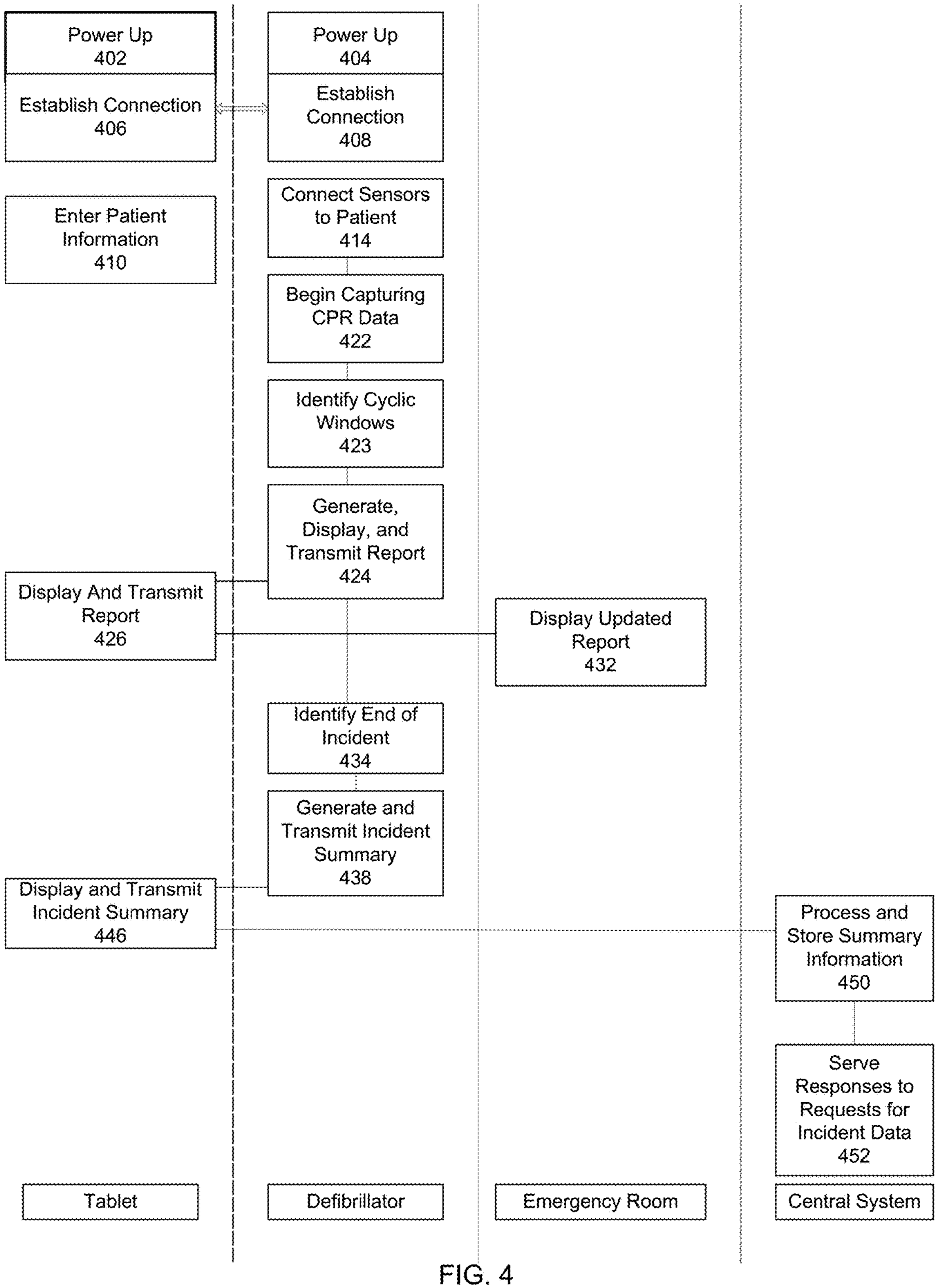
FIG. 4 is a swim lane diagram of a process for sharing CPR performance data between various sub-systems in a larger healthcare system.
Figure 5:
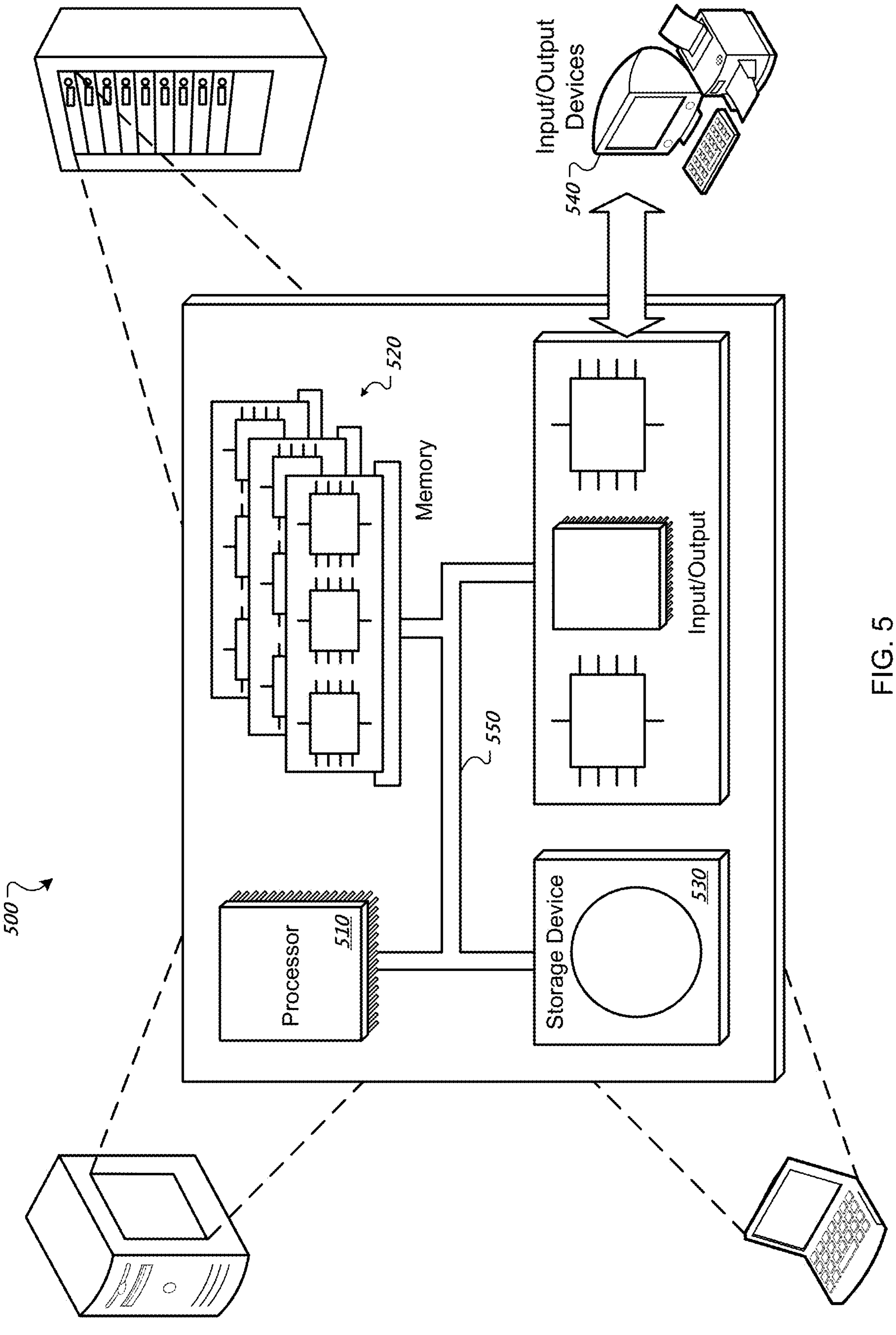
FIG. 5 shows an example of a generic computer device and a generic mobile computer device, which may be used with the techniques described here.

FIG. 4 is a swim lane diagram of a process for sharing CPR performance data between various sub-systems in a larger healthcare system. In general, the process discussed here is similar to those discussed above, though actions performed on particular components of a larger system are shown in more detail to indicate examples of a manner in which such actions may be performed in one implementation.

The process begins at an accident scene, were a rescuer has deployed equipment from a rescue vehicle, such as a defibrillator and an associated computing device such as a tablet computer, that may communicate with the defibrillator through a wireless data connection. At boxes 402, 404, the two devices are powered up by the rescuer, and when they have performed initial activities to become active, they may automatically establish a data connection, such as by performing BLUETOOTH pairing between the devices (boxes 406, 408). The rescuer may then enter patient information, at box 410, into the tablet computer, such as basic information regarding the condition of the patient, blood pressure and pulse for the patient, and gender of the patient. Information such as blood pressure and pulse may be recorded automatically by the tablet, such as by way of wired or wireless connection with tools for taking the victim's blood pressure and pulse.

At box 414, the rescuer connects sensors to the patient. For example, the rescuer may open a short of a patient and place defibrillation pads on the patient. The defibrillation pads may also include ECG electrodes for sensing cardiac activity of the patient. At this point, the defibrillator may begin performing according to standard protocols for delivering care to a patient, such as by analyzing cardiac activity of the patient. Such action may also lead to the rescuer performing chest compressions and other CPR activities on the patient. Thus, at box 422, the defibrillator may begin capturing CPR data, such as depth and rate of compressions data and other data discussed above. Also, the defibrillator may identify the beginning point for each interval or cycle in the performance of CPR, so as to associate the data with a particular cycle. At box 424, the defibrillator generates, displays, and transmits a report regarding data that is being captured from the performance of CPR. Such a report may take a variety of forms. For example, the report may simply indicate initial or primary parameters that are being captured in real time, and the reporting for those parameters may be continuously updated such as every second or portion of a second. Later, the report may include such real-time data, but may also include summarized, secondary data for one or more CPR intervals or for an entire time period of an incident.

At various points in time, the defibrillator may also transfer data for generating similar reports to the tablet computer, and the tablet computer may display information related to the provision of CPR to the patient, and may also to further transmit the data to a computing device in n area of an emergency room where the victim is to be taken (box 426). The information may then be displayed as a report in the emergency room. The report for the emergency room may take the same form or different forms than that shown on the defibrillator or the tablet computer. For example, if one is to assume that the viewer in the emergency room can give less attention to the report than can the rescuer, the emergency room report may provide less information and be updated less frequently than is the report on the defibrillator or the tablet computer. Particular values that are shown in each report, the frequency with which they are updated, the manner in which they are displayed, and the order in which they are displayed may vary depending on the particular application and the needs of the particular users.

At box 434, the defibrillator identifies that the incident has ended. For example, if no ECG signals are received for a predetermined period of time, the defibrillator may assume that it has been disconnected from the victim and that it will not be used on the victim again. Other mechanisms for determining that an incident has ended are discussed above. When such a determination is made, the defibrillator may transfer its remaining data to the tablet computer and may also generate a summary of the incident and transmit that summary to the tablet computer (box 438). At box 446, the tablet computer displays the summary and also transmits information for the summary to a central server system. Such transmission may be directed toward providing a semi-permanent or permanent record regarding the care that was provided to the victim.

Thus, at box 450, the central server system processes the information received from the tablet computer and stores information about the incident. In certain embodiments, all or substantially all of the information captured by the defibrillator may be stored. Where space limitations or other considerations prevail, summary information may be stored. For example, average values for various parameters may be stored for each cardiac or CPR interval, rather than storing raw values for much smaller but more numerous time segments within each interval.

At some later date, the rescuer or another individual may be interested in analyzing the data that was saved for the particular incident or a group of incidents. Therefore, at box 452, when such a request is received by the central server system, the system may serve responses to the request for data about the incident or other incidents. At the time of serving the data for the incident, the central server system may generate one or more additional reports for presenting the information about the incident or incidents. For example, graphs for each incident at which a particular rescuer acted may be displayed side-by-side, and trend lines or other trend features may be displayed, so that the progression in the skills of a rescuer may be judged, and a reviewer or the rescuer may determine whether the rescuer needs to adjust his or her approach to providing care in a rescue situation.

FIG. 4 shows an example of a generic computer device 400 and a generic mobile computer device 450, which may be used with the techniques described here. Computing device 400 is intended to represent various forms of digital computers, such as laptops, desktops, workstations, personal digital assistants, servers, blade servers, mainframes, and other appropriate computers. Computing device 450 is intended to represent various forms of mobile devices, such as personal digital assistants, cellular telephones, smartphones, and other similar computing devices. The components shown here, their connections and relationships, and their functions, are meant to be exemplary only, and are not meant to limit implementations of the inventions described and/or claimed in this document.

Computing device 400 includes a processor 402, memory 404, a storage device 506, a high-speed interface 408 connecting to memory 404 and high-speed expansion ports 410, and a low speed interface 412 connecting to low speed bus 414 and storage device 406. Each of the components 402, 404, 406, 408, 410, and 412, are interconnected using various busses, and may be mounted on a common motherboard or in other manners as appropriate. The processor 402 can process instructions for execution within the computing device 400, including instructions stored in the memory 404 or on the storage device 406 to display graphical information for a GUI on an external input/output device, such as display 416 coupled to high speed interface 408. In other implementations, multiple processors and/or multiple buses may be used, as appropriate, along with multiple memories and types of memory. Also, multiple computing devices 400 may be connected, with each device providing portions of the necessary operations (e.g., as a server bank, a group of blade servers, or a multi-processor system).

The memory 404 stores information within the computing device 4500. In one implementation, the memory 404 is a volatile memory unit or units. In another implementation, the memory 404 is a non-volatile memory unit or units. The memory 404 may also be another form of computer-readable medium, such as a magnetic or optical disk.

The storage device 406 is capable of providing mass storage for the computing device 400. In one implementation, the storage device 406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 404, the storage device 406, memory on processor 402, or a propagated signal.

The high speed controller 408 manages bandwidth-intensive operations for the computing device 400, while the low speed controller 412 manages lower bandwidth-intensive operations. Such allocation of functions is exemplary only. In one implementation, the high-speed controller 408 is coupled to memory 4504, display 416 (e.g., through a graphics processor or accelerator), and to high-speed expansion ports 410, which may accept various expansion cards (not shown). In the implementation, low-speed controller 412 is coupled to storage device 406 and low-speed expansion port 414. The low-speed expansion port, which may include various communication ports (e.g., USB, BLUETOOTH, Ethernet, wireless Ethernet) may be coupled to one or more input/output devices, such as a keyboard, a pointing device, a scanner, or a networking device such as a switch or router, e.g., through a network adapter.

The computing device 400 may be implemented in a number of different forms, as shown in the figure. For example, it may be implemented as a standard server 420, or multiple times in a group of such servers. It may also be implemented as part of a rack server system 424. In addition, it may be implemented in a personal computer such as a laptop computer 422. Alternatively, components from computing device 400 may be combined with other components in a mobile device (not shown), such as device 450. Each of such devices may contain one or more of computing device 400, 450, and an entire system may be made up of multiple computing devices 400, 450 communicating with each other.

Computing device 450 includes a processor 452, memory 464, an input/output device such as a display 454, a communication interface 466, and a transceiver 468, among other components. The device 450 may also be provided with a storage device, such as a micro drive or other device, to provide additional storage. Each of the components 450, 452, 464, 454, 466, and 468, are interconnected using various buses, and several of the components may be mounted on a common motherboard or in other manners as appropriate.

The processor 452 can execute instructions within the computing device 450, including instructions stored in the memory 464. The processor may be implemented as a chipset of chips that include separate and multiple analog and digital processors. The processor may provide, for example, for coordination of the other components of the device 450, such as control of user interfaces, applications run by device 450, and wireless communication by device 450.

Processor 452 may communicate with a user through control interface 458 and display interface 456 coupled to a display 454. The display 454 may be, for example, a TFT LCD (Thin-Film-Transistor Liquid Crystal Display) or an OLED (Organic Light Emitting Diode) display, or other appropriate display technology. The display interface 456 may comprise appropriate circuitry for driving the display 454 to present graphical and other information to a user. The control interface 458 may receive commands from a user and convert them for submission to the processor 452. In addition, an external interface 462 may be provide in communication with processor 452, so as to enable near area communication of device 450 with other devices. External interface 462 may provide, for example, for wired communication in some implementations, or for wireless communication in other implementations, and multiple interfaces may also be used.

The memory 464 stores information within the computing device 450. The memory 464 can be implemented as one or more of a computer-readable medium or media, a volatile memory unit or units, or a non-volatile memory unit or units. Expansion memory 474 may also be provided and connected to device 450 through expansion interface 472, which may include, for example, a SIMM (Single In Line Memory Module) card interface. Such expansion memory 474 may provide extra storage space for device 450, or may also store applications or other information for device 450. Specifically, expansion memory 474 may include instructions to carry out or supplement the processes described above, and may include secure information also. Thus, for example, expansion memory 474 may be provide as a security module for device 450, and may be programmed with instructions that permit secure use of device 450. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 464, expansion memory 474, memory on processor 452, or a propagated signal that may be received, for example, over transceiver 468 or external interface 462.

Device 450 may communicate wirelessly through communication interface 466, which may include digital signal processing circuitry where necessary. Communication interface 466 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 468. In addition, short-range communication may occur, such as using a BLUETOOTH, WiFi, or other such transceiver (not shown). In addition, GPS (Global Positioning System) receiver module 470 may provide additional navigation- and location-related wireless data to device 450, which may be used as appropriate by applications running on device 450.

Device 450 may also communicate audibly using audio codec 460, which may receive spoken information from a user and convert it to usable digital information. Audio codec 460 may likewise generate audible sound for a user, such as through a speaker, e.g., in a handset of device 450. Such sound may include sound from voice telephone calls, may include recorded sound (e.g., voice messages, music files, etc.) and may also include sound generated by applications operating on device 450.

The computing device 450 may be implemented in a number of different forms, as shown in the figure. For example, it may be implemented as a cellular telephone 480. It may also be implemented as part of a smartphone 482, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the invention. For example, much of this document has been described with respect to ICU monitoring with attending physicians, but other forms of patient monitoring and reporting may also be addressed.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A system for monitoring care provided for a patient, the system comprising:

at least one medical device configured to provide defibrillation to the patient, the at least one medical device comprising:

at least one resuscitation activity sensor configured to receive signals representative of a resuscitation activity performed for the patient by a rescuer;

at least one physiological sensor configured to receive signals representative of physiology of the patient;

a medical device display; and at least one medical device processor electrically connected to the at least one resuscitation activity sensor, the at least one physiological sensor, and the medical device display, wherein the at least one medical device processor is configured to:

receive and process the signals from the at least one resuscitation activity sensor and from the at least one physiological sensor, determine at least one resuscitation activity parameter for the resuscitation activity performed for the patient based, at least in part, on the processed signals from the at least one resuscitation activity sensor, cause feedback guidance based on the determined at least one resuscitation activity parameter, which guides the rescuer to perform the resuscitation activity within a predetermined target range for the at least one resuscitation activity parameter, to be displayed in real time on the medical device display, and transmit data representative of the feedback guidance and data representative of the physiology of the patient determined from the signals received from the at least one physiological sensor to at least one local portable computing device; and the at least one local portable computing device comprising a portable computing device display, a short-range wireless transceiver configured to transmit data over a small area network, an interface for receiving a user input, and at least one portable computing device processor, wherein the at least one portable computing device processor is configured to:

receive with the short-range wireless transceiver the data representative of the feedback guidance and the data representative of the physiology of the patient from the at least one medical device, receive patient information input via the interface of the at least one portable computing device, and cause the feedback guidance to be displayed in real time on the portable computing device display simultaneous with the feedback guidance displayed on the medical device display and together with the data representative of the physiology of the patient and with at least one visual indication representative of the received patient information.

2. The system of claim 1, wherein the at least one local portable computing device comprises a cellular telephone, a smartphone, a personal digital assistant, or a computer tablet.

3. The system of claim 1, wherein the portable computing device display displays the real-time feedback guidance and historical information about performance of the resuscitation activity for the patient.

4. The system of claim 1, wherein the at least one local portable computing device further comprises at least one speaker, and wherein the at least one portable computing device processor is configured to cause the at least one speaker to emit audio feedback guidance for the resuscitation activity simultaneous with the feedback guidance displayed on the medical device display and the portable computing device display.

5. The system of claim 1, wherein the at least one portable computing device processor is configured to receive patient information manually input by a user of the at least one local portable computing device and to transmit the patient information from the at least one local portable computing device to the at least one medical device.

6. The system of claim 1, wherein the at least one resuscitation activity sensor comprises a chest compression sensor or an airflow sensor for sensing ventilation airflow provided to the patient.

7. The system of claim 1, wherein the at least one resuscitation activity parameter comprises at least one of depth of chest compressions, rate of chest compressions, chest compression fraction, ventilation volume, ventilation rate, pre-shock delay, post-shock delay, or patient perfusion percentage.

8. The system of claim 1, wherein the at least one medical device comprises a defibrillator comprising at least one therapeutic electrode configured to be connected to the patient for providing cardiac treatment for the patient.

9. The system of claim 1, wherein the at least one resuscitation activity sensor of the medical device comprises an airflow sensor, wherein the at least one local portable computing device is in wireless communication with the airflow sensor to measure information representative of ventilations provided to the patient, and wherein the at least one portable computing device processor is configured to receive and process signals from the airflow sensor, determine at least one ventilation parameter based on the received and processed signals from the airflow sensor, and cause the portable computing device display to display ventilation feedback guidance based on the determined at least one ventilation parameter.

10. The system of claim 9, wherein the at least one resuscitation activity sensor of the at least one medical device further comprises a chest compression sensor configured to detect chest compressions provided for the patient by the rescuer, and wherein the portable computing device display simultaneously displays chest compression feedback guidance and the ventilation feedback guidance.

11. The system of claim 1, wherein the at least one local portable computing device processor is configured to determine at least one patient physiological parameter based on the signals detected by the at least one patient physiological sensor.

12. The system of claim 11, wherein the at least one portable computing device processor is configured to cause a visual indication representative of the at least one patient physiological parameter to be displayed on the portable computing device display.

13. The system of claim 12, wherein the at least one local portable computing device processor is configured to cause the visual indication representative of the at least one patient physiological parameter and another visual indication representative of the at least one resuscitation activity parameter to be displayed on the portable computing device display along with the feedback guidance.

14. The system of claim 13, wherein the compression feedback guidance and the ventilation feedback guidance are displayed simultaneously on the portable computing device display.

15. The system of claim 1, wherein the at least one physiological sensor is configured to detect signals representative of at least one of patient blood oxygen level, patient blood pressure, patient oxygen saturation ($SPO_2$), patient end-tidal $CO_2$, or patient heart rate.

16. The system of claim 1, wherein the at least one resuscitation activity sensor of the medical device comprises an airflow sensor, wherein the at least one medical device processor is in wireless communication with the airflow sensor to measure information representative of ventilations provided to the patient, and wherein the at least one medical device processor is configured to receive and process signals from the airflow sensor and determine at least one ventilation parameter based on the received and processed signals from the airflow sensor.

17. The system of claim 16, wherein the at least one medical device processor is configured to transmit data representative of the determined at least one ventilation parameter to the at least one local portable computing device, and wherein the at least one portable computing device processor is configured to receive the data representative of the determined at least one ventilation parameter from the at least one medical device, and cause the portable computing device display to display ventilation feedback guidance based on the determined at least one ventilation parameter.

18. The system of claim 1, wherein the patient information comprises a measured value for at least one vital sign of the patient.

19. The system of claim 1, wherein the patient information comprises a measured value for at least one of a blood pressure or heart rate of the patient.

20. The system of claim 1, wherein the patient information comprises at least one of patient gender, patient allergies, or medications taken by the patient.

21. A system for monitoring care provided for a patient, the system comprising:

at least one medical device comprising:

at least one chest compression sensor configured to receive chest compression signals representative of chest compressions performed for the patient by a first rescuer;

at least one airflow sensor configured to receive airflow signals representative of ventilation airflow provided to the patient by a second rescuer;

at least one physiological sensor configured to receive signals representative of physiology of the patient;

a medical device display;

a medical device wireless transceiver; and at least one medical device processor electrically connected to the at least one chest compression sensor, the at least one airflow sensor, the at least one physiological sensor, and the medical device display, wherein the at least one medical device processor is configured to:

receive and process the chest compression signals from the at least one chest compression sensor, the airflow signals from the at least one airflow sensor, and the signals representative of physiology of the patient from the at least one physiological sensor, determine at least one chest compression parameter for the chest compressions performed for the patient based, at least in part, on the processed chest compression signals, determine at least one ventilation parameter for the ventilation airflow provided to the patient based, at least in part, on the processed airflow signals, cause feedback guidance comprising at least one visual indicator derived from the determined at least one chest compression parameter and the determined at least one ventilation parameter to be displayed in real time on the medical device display, and cause the medical device wireless transceiver to wirelessly transmit data representative of the feedback guidance, data representative of patient ventilation determined from the airflow signals, and data representative of the physiology of the patient determined from the signals received from the at least one physiological sensor to at least one local portable computing device; and the at least one local portable computing device comprising a portable computing device display, a portable computing device wireless transceiver, which receives wireless data transmissions from the medical device wireless transceiver, and at least one portable computing device processor, wherein the at least one portable computing device processor is configured to:

receive the data representative of the feedback guidance, the data representative of patient ventilation, and the data representative of the physiology of the patient from the at least one medical device, and cause the feedback guidance comprising the at least one visual indicator derived from the determined at least one chest compression parameter and the determined at least one ventilation parameter to be displayed in real time on the portable computing device display.

22. The system of claim 21, wherein the medical device wireless transceiver and the portable computing device wireless transceiver transmit data over a small area wireless network.

23. The system of claim 21, wherein the portable computing device wireless transceiver comprises a short-range data transceiver and a long-range data transceiver, and wherein the at least one portable computing device processor is configured to receive the wireless data transmissions from the at least one medical device via the short-range transceiver and transmit information about the patient or the care provided for the patient to a remote computer network or device with the long-range wireless transceiver.

24. The system of claim 21, wherein the feedback guidance is displayed simultaneously on the medical device display and the portable computing device display.

* * * * *